(12) United States Patent
Ding (10) Patent No.: US 10,145,769 B2
(45) Date of Patent: Dec. 4, 2018

(54) DILUTION AND FILTRATION DEVICE, APPARATUS AND METHOD OF PREPARING EXCREMENT DETECTION SOLUTIONS

(71) Applicant: AVE SCIENCE & TECHNOLOGY CO., LTD., Changsha (CN)

(72) Inventor: Jianwen Ding, Changsha (CN)

(73) Assignee: AVE SCIENCE & TECHNOLOGY CO., LTD., Changsha, Hunan (CN)

( * ) Notice: Subject to any disclaimer, the term of this patent is extended or adjusted under 35 U.S.C. 154(b) by 185 days.

(21) Appl. No.: 15/200,979

(22) Filed: Jul. 1, 2016

(65) Prior Publication Data

US 2016/0313226 A1    Oct. 27, 2016

Related U.S. Application Data (63) Continuation of application No. PCT/CN2014/071530, filed on Jan. 27, 2014.

(30) Foreign Application Priority Data

Jan. 2, 2014   (CN) .......................... 2014 1 0000964

(51) Int. Cl.
*G01N 1/38* (2006.01)
*A61B 10/00* (2006.01)
*B01F 7/00* (2006.01)

(52) U.S. Cl.
CPC .......... *G01N 1/38* (2013.01); *A61B 10/0038* (2013.01); *B01F 7/00333* (2013.01); *B01L 2300/0681* (2013.01)

(58) Field of Classification Search
CPC ............. A61B 10/0038; B01F 7/00333; B01L 2300/0681; G01N 1/38
See application file for complete search history.

(56) References Cited

U.S. PATENT DOCUMENTS

| | | | | |
|---|---|---|---|---|
| 4,116,066 A | * | 9/1978 | Mehl .................... | A61B 10/007 600/573 |
| 4,439,319 A | * | 3/1984 | Rock .................. | A61B 10/0096 210/238 |
| 4,849,173 A | * | 7/1989 | Chang ................ | A61B 10/0038 422/422 |
| 5,431,884 A | * | 7/1995 | McDonough ...... | A61B 10/0038 209/17 |

(Continued)

*Primary Examiner* — Daniel S Larkin
(74) *Attorney, Agent, or Firm* — Flener IP & Business Law; Zareefa B. Flener (57) ABSTRACT

A dilution and filtration device comprises: a sampling member comprising a suspension collecting chamber having at least one suspension collecting window disposed at a side surface of the suspension collecting chamber; a top cap having a through hole at a center portion of the top cap; a connecting cylinder disposed at a top end of the sampling member and mounted to the through hole of the top cap such that the connecting cylinder is concentric with the through hole and is rotatable; and a specimen tube connected to the top cap and accommodating the sampling member. An apparatus of preparing excrement detection solutions comprising the dilution and filtration device and a method of preparing excrement detection solutions using the dilution and filtration device are also provided.

16 Claims, 8 Drawing Sheets

(56) References Cited

U.S. PATENT DOCUMENTS

| | | | | |
|---|---|---|---|---|
| 5,624,554 | A | * | 4/1997 | Faulkner ............ A61B 10/0038 |
| | | | | 210/232 |
| 6,582,665 | B2 | * | 6/2003 | Faulkner ............ A61B 10/0096 |
| | | | | 210/233 |
| 7,338,634 | B2 | * | 3/2008 | Chang ................ A61B 10/0038 |
| | | | | 422/408 |
| 7,758,815 | B2 | * | 7/2010 | Hartselle ............ A61B 10/0096 |
| | | | | 422/400 |
| 2004/0031333 | A1 | * | 2/2004 | Buckner, III ........ B01F 7/0015 |
| | | | | 73/863 |
| 2006/0115385 | A1 | * | 6/2006 | Jon Meyer ......... A61B 10/0096 |
| | | | | 422/547 |
| 2010/0285520 | A1 | * | 11/2010 | Halverson ............ B01L 3/5029 |
| | | | | 435/30 |

* cited by examiner

DILUTION AND FILTRATION DEVICE, APPARATUS AND METHOD OF PREPARING EXCREMENT DETECTION SOLUTIONS

CROSS-REFERENCE TO RELATED APPLICATIONS

This application is a continuation of international application No. PCT/CN2014/071530 filed on Jan. 27, 2014, which claims the benefit and priority of Chinese patent application No. 201410000964.6 filed on Jan. 2, 2014. Both of these applications are incorporated herein in their entirety by reference.

TECHNICAL FIELD

Embodiments of the present invention relate to a dilution and filtration device, an apparatus of preparing excrement detection solutions and a method of preparing excrement detection solutions.

BACKGROUND

Excrement detection is one of main detection items to detect a patient's conditions. Generally, before formed elements of excrement are detected, some operations such as dilution, filtration and sampling should be performed using an apparatus of preparing excrement detection solutions so as to obtain suspensions for formed element detection. Specifically, firstly excrement specimens are collected and placed in a dilution and filtration device which is a part of an apparatus of preparing excrement detection solutions, and then the dilution and filtration device receiving the excrement specimens is mounted to a stirring and sampling device which is the other part of the apparatus of preparing excrement detection solutions. Afterwards, the excrement specimens are diluted, stirred, filtrated and sampled to obtain specimens to be detected in a detection device.

SUMMARY

Embodiments of the present invention provide a dilution and filtration device having a reduced size.

In accordance with one or more embodiments of the present invention, a dilution and filtration device comprises: a sampling member comprising a suspension collecting chamber having at least one suspension collecting window disposed at a side surface of the suspension collecting chamber; a top cap having a through hole at a center portion of the top cap; a connecting cylinder disposed at a top end of the sampling member and mounted to the through hole of the top cap such that the connecting cylinder is concentric with the through hole and is rotatable; and a specimen tube connected to the top cap and accommodating the sampling member.

The dilution and filtration device may further comprise at least one filtering net disposed at the at least one suspension collecting window.

The sampling member may further comprise at least one extended plate which is perpendicular to the side surface of the suspension collecting chamber where the at least one suspension collecting window is located.

The suspension collecting chamber may have a shape of a hollow rectangle, the sampling member may comprise two suspension collecting windows disposed at opposite side surfaces of the suspension collecting chamber respectively and two extended plates which are perpendicular to the two opposite side surfaces of the suspension collecting chamber where the two suspension collecting windows are located respectively.

The dilution and filtration device may comprise two filtering nets disposed at the two suspension collecting windows respectively. One filtering net may have a larger size and a larger aperture and is disposed at a higher position while the other filtering net may have a smaller size and a smaller aperture and is disposed at a lower position.

The connecting cylinder may be clearance fixed to the through hole of the top cap.

The top cap and the specimen tube may be threaded connected to each other.

The specimen tube may comprise a plurality of protrusion ribs transversely protruding from an inner wall of the specimen tube and extending along a longitudinal axis of the specimen tube.

The dilution and filtration device may further comprise a soft film covering the through hole of the top cap.

The sampling member may further comprise a collecting end disposed at a bottom end of the sampling member. The collecting end may have a shape of any of a three-edged rule, a ladle shape, a tooth shape, a brush shape and a mace shape.

The dilution and filtration device may further comprise a blocking member which is disposed at the top end of the sampling member and below the connecting cylinder. The connecting cylinder and the blocking member may be detachably connected to the sampling member. The connecting cylinder and the blocking member may be clamping connected to the sampling member.

In accordance with one or more embodiments of the present invention, an apparatus of preparing excrement detection solutions comprises a dilution and filtration device and a stirring and sampling device. The dilution and filtration device comprises: a sampling member comprising a suspension collecting chamber having at least one suspension collecting window disposed at a side surface of the suspension collecting chamber; a top cap having a through hole at a center portion of the top cap; a connecting cylinder disposed at a top end of the sampling member and mounted to the through hole of the top cap such that the connecting cylinder is concentric with the through hole and is rotatable; and a specimen tube connected to the top cap and accommodating the sampling member. The stirring and sampling device comprises: a vertical movement part comprising a vertical driving motor, a rack driven by the vertical driving motor and a transmission gear engaged with the rack; a stirring part connected to the vertical movement part and comprising a cylinder stirring handle which has a shape matching an inner shape of the connecting cylinder; and a sampling needle passing through an inner chamber of the cylinder stirring handle and connected to the vertical movement part.

The stirring part may further comprise a fixed shaft disposed between the cylinder stirring handle and the vertical movement part, and the sampling needle may further pass through an inner chamber of the fixed shaft.

The sampling member may further comprise at least one extended plate which is perpendicular to the side surface of the suspension collecting chamber where the at least one suspension collecting window is located.

The sampling member may comprise a plurality of suspension collecting windows disposed at side surfaces of the suspension collecting chamber, and a plurality of extended plates which are perpendicular to the side surfaces of the suspension collecting chamber where the plurality of suspension collecting windows are located respectively.

In accordance with one or more embodiments of the present invention, a method of preparing excrement detection solutions using the above-mentioned dilution and filtration comprises: mounting the connecting cylinder to the sampling member and the through hole of the top cap; collecting excrement specimens by the sampling member, placing the sampling member into the specimen tube, and connecting the specimen tube to the top cap; injecting dilution solutions into the suspension collecting chamber and stirring suspensions formed by mixing of the excrement specimens and the dilution solutions; and sucking the suspensions during stirring from the suspension collecting chamber to obtain the excrement detection solutions.

According to embodiments of the present invention, the sampling member, the connecting cylinder and the through hole are concentric, i.e., they have a same axis. In this way, only the through hole is disposed at the top cap, thus an area of the top cap is reduced and the whole size of the dilution and filtration device is reduced accordingly.

In addition, since the sampling member, the connecting cylinder and the through hole are coaxial, it is just required to align the sampling needle with the center portion of the top cap, thus the difficulty to install the dilution and filtration device on an apparatus of preparing excrement detection solutions is reduced.

Furthermore, the formed elements in the suspensions are collected by rotation of the sampling member, thus the connection effect is ensured, which is beneficial to the following detection operations.

BRIEF DESCRIPTION OF DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like or similar elements throughout. In this regard, the present embodiments may have different forms and should not be construed as being limited to the descriptions set forth herein. Accordingly, the embodiments are merely described below, by referring to the figures, to explain aspects of the present description.

Figure 1:
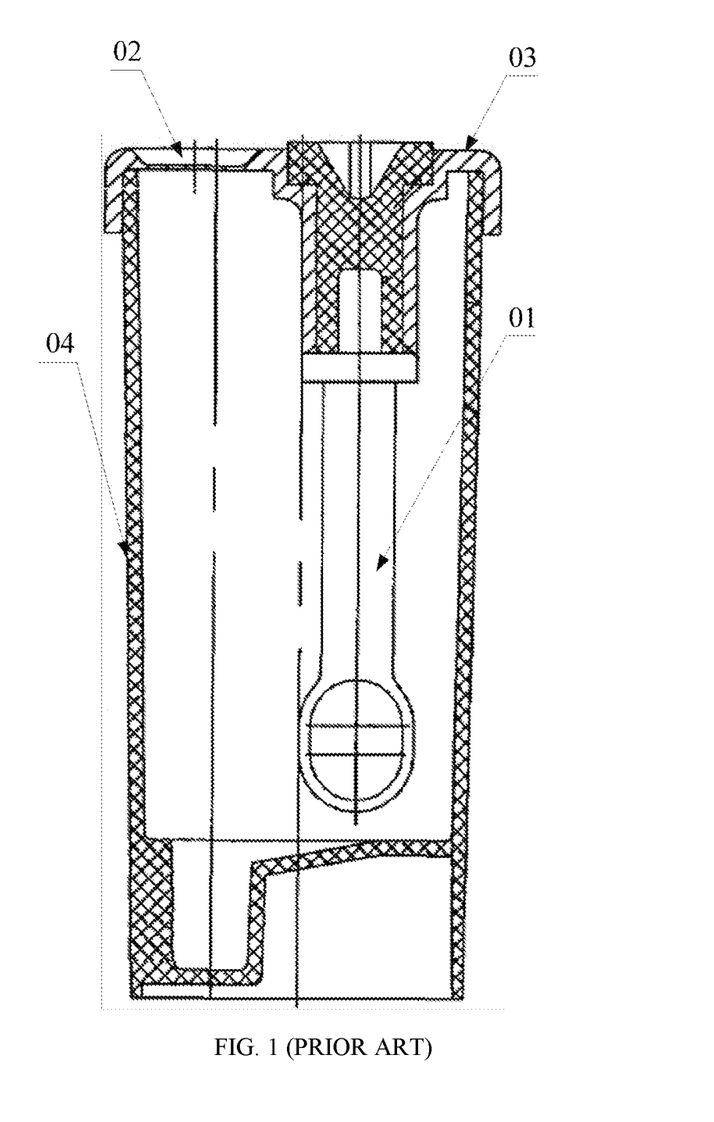
FIGS. 1 and 2 are schematic views illustrating structures of two different dilution and filtration devices according to the prior art.
Figure 2:
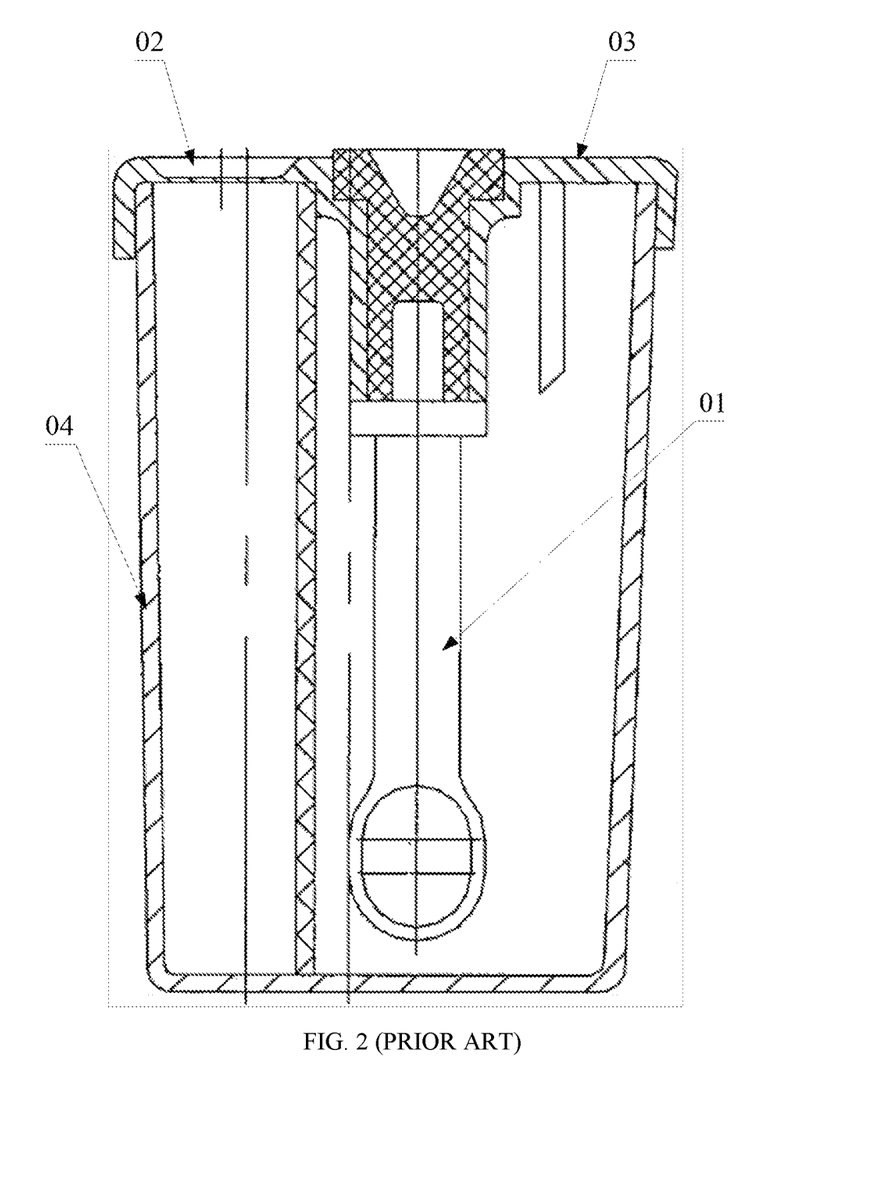

FIGS. 1 and 2 are schematic views illustrating structures of two different dilution and filtration devices according to the prior art. As shown in FIGS. 1 and 2, in each of dilution and filtration devices according to the prior art, a specimen tube 04, a top cap 03 and a sampling member 01 are included. The top cap 03 has an insertion hole 02. The sampling member 01 is a sampling ladle used to place excrement specimens into the specimen tube 04. After dilution solutions are injected into the specimen tube 04 by a sampling needle (not shown) through the insertion hole 2, the sampling member 01 is rotated, so that suspensions formed by mixing of the dilution solutions and the excrement specimens are stirred. And then the suspensions after stirring are sucked by the sampling needle through the insertion hole 02.

In the prior art, both of the insertion hole 02 and the sampling member 01 are disposed in the top cap 03 at different positions, thus the top cap 03 should have a large area to accommodate both of them. Similarly, the specimen tube 04 should have a large cross-sectional area to ensure operations such as dilution and sampling. Therefore, the dilution and filtration devices have large sizes. In addition, the insertion hole 02 is not concentric with the top cap 03 and the specimen tube 04, it is difficult to install the dilution and filtration device on an apparatus of preparing excrement detection solutions to make the sampling needle be aligned with the insertion hole 02.

In order to resolve the above-described problems, a new dilution and filtration device with a reduced size is provided according to embodiments of the present invention.

Figure 3:
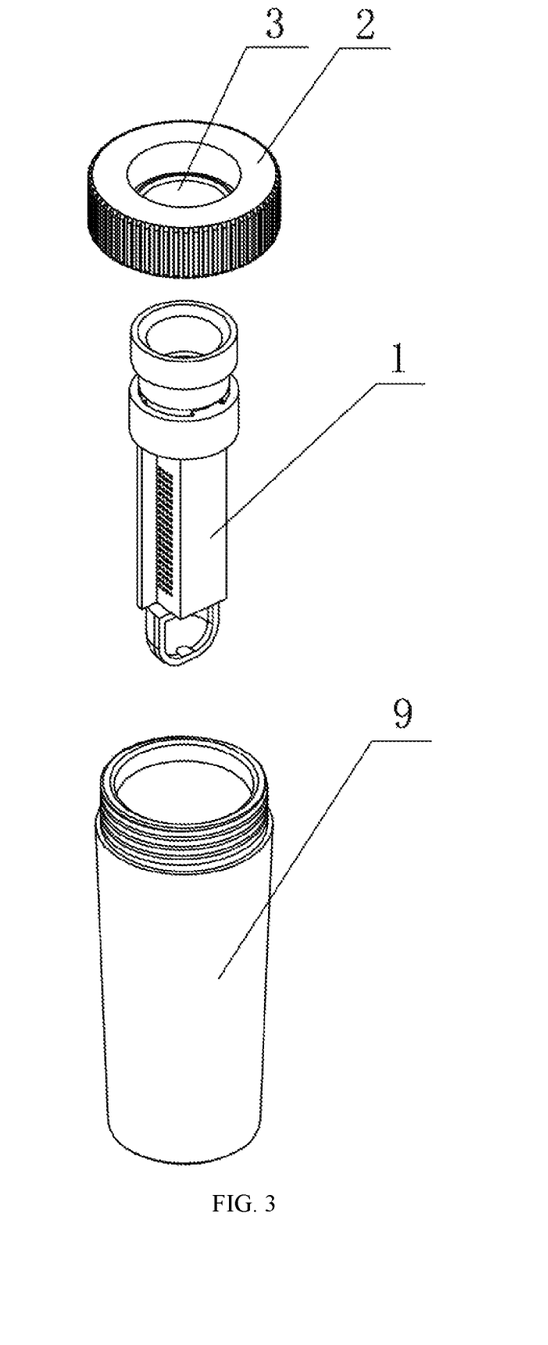
FIG. 3 is an exploded perspective view illustrating a dilution and filtration device according to an embodiment of the present invention.
Figure 5:
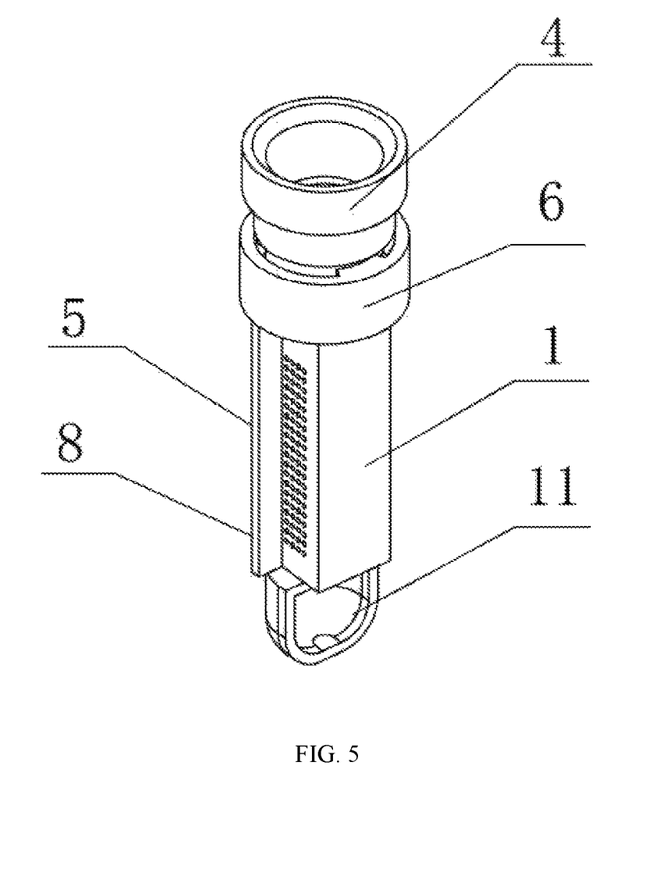
FIG. 5 is a schematic view illustrating a structure of a sampling member.
Figure 6:
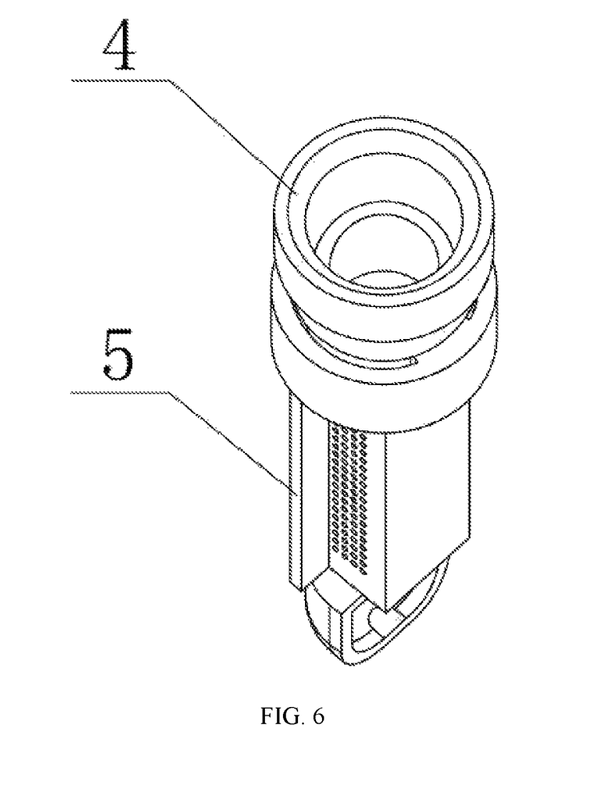
FIG. 6 is a schematic view illustrating the structure of the sampling member from another angle.

FIG. 3 is an exploded perspective view illustrating a dilution and filtration device according to an embodiment of the present invention; FIGS. 5 and 6 are schematic views illustrating a structure of a sampling member of the dilution and filtration device from different angles.

As shown in FIGS. 3, 5 and 6, a dilution and filtration device according to an embodiment of the present invention comprises a sampling member 1, a top cap 2, a connecting cylinder 4 and a specimen tube 9.

The top cap 2 has a shape of cylinder as a whole, and has a circular through hole 3 at a center portion thereof. The through hole 3 is used to connect the top cap 2 and the sampling member 1, and also functions as a passage through which a sampling needle 12 (referring to FIG. 8) enters into the dilution and filtration device.

A side wall of a circular groove disposed at a bottom end of the top cap 2 has internal screw threads, which can be engaged with external screw threads provided on an outer wall of a top end of the specimen tube 9. In this way, the top cap 2 can be connected with the specimen tube 9 through a threaded connection, i.e., through their respective internal and external screw threads.

The connecting cylinder 4 is disposed at a top end of the sampling member 1, e.g., clamping connected to the sampling member 1 at the top end of the sampling member 1, and mounted to, e.g., clearance fixed to, the through hole 3 of the top cap 2, so that the sampling member 1, the connecting cylinder 4 and the through hole 3 are concentric after assembling. The connection between the connecting cylinder 4 and the sampling member 1 may be detachable. The connecting cylinder 4 has a hollow chamber and can cooperate with a stirring handle 13 (referring to FIG. 8) which will be described later, so that suspensions in the specimen tube 9 can be stirred. In addition, the connecting cylinder 4 also functions as clamping the sampling member 1 to ensure the sampling member 1 not falling into a bottom end of the specimen tube 9.

In the dilution and filtration device according to this embodiment of the present invention, the through hole 3 is disposed at the center portion of the top cap 2, the connecting cylinder 4 detachably connected with the sampling member 1 is clearance fixed to the through hole 3 of the top cap 2, meanwhile the sampling member 1, the connecting cylinder 4 and the through hole 3 are concentric, so that the sampling member 1 can be rotated freely with respect to its axis to stir the suspensions. In addition, after the top cap 2 is mounted on the specimen tube 9, the sampling member 1 can be accommodated in the specimen tube 9 completely.

In the sampling operation, firstly specimens are collected by the sampling member 1 and placed in the specimen tube 9, and then the sampling needle 12 sucks dilution solutions, and injects the dilution solutions into the sampling member 1 through the through hole 3. Then the connecting cylinder 4 is rotated and the sampling member 1 is rotated accordingly, so that suspensions formed by mixing of the specimens and the dilution solutions are stirred. After stirring, the sampling needle 12 sucks the suspensions inside the specimen tube 9 to accomplish the sampling operation.

Unlike the prior art in which the sampling member 01 and the insertion hole 02 are disposed at the top cap 03 side by side, in this embodiment, the sampling member 1, the connecting cylinder 4 and the through hole 3 are concentric, i.e., they have the same axis. In this way, only the through hole 3 is disposed at the top cap 2, thus an area of the top cap 2 is reduced and the whole size of the dilution and filtration device is reduced accordingly.

In addition, since the sampling member 1, the connecting cylinder 4 and the through hole 3 are coaxial, it is just required to align the sampling needle 12 with the center portion of the top cap 2, thus the difficulty to install the dilution and filtration device on an apparatus of preparing excrement detection solutions is reduced.

Furthermore, in this embodiment, the formed elements in the suspensions are collected by rotation of the sampling member 1, thus the connection effect is ensured, which is beneficial to the following detection operations.

In another embodiment of the present invention, referring to FIGS. 3, 5 and 6, a blocking member 6 which is disposed at the top end of the sampling member 1 is further included. For example, the blocking member 6 is clamping connected to the sampling member 1 at the top end of the sampling member 1. The connection between the blocking member 6 and the sampling member 1 may be detachable. The blocking member 6 is located below the connecting cylinder 4 and is used to prevent the sampling member 1 from falling out the specimen tube 9 when the dilution and filtration device is turned over or tilted.

Figure 4:
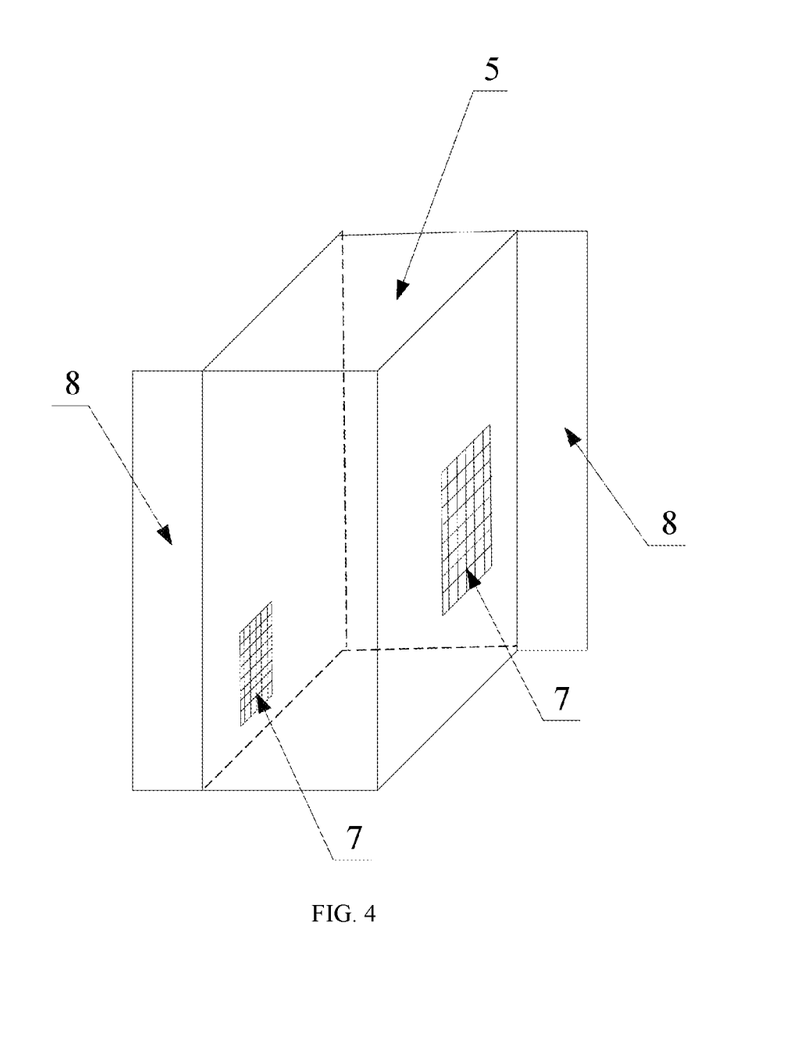
FIG. 4 is a schematic view illustrating operations of extended plates.

In another embodiment of the present invention, referring to FIG. 4 which illustrates operations of extended plates and further referring to FIGS. 5 and 6, the sampling member 1 includes a suspension collecting chamber 5, and also includes a plurality of suspension collecting windows disposed at side walls of the suspension collecting chamber 5 respectively so that the suspensions in the specimen tube 9 can enter into the suspension collecting chamber 5 through the suspension collecting windows. The suspension collecting chamber 5 has a shape of a rectangle, which is beneficial to stirring of suspensions.

In this embodiment, there are two suspension collecting windows located at opposite side surfaces of the rectangular suspension collecting chamber 5 respectively, but this invention is not limited thereto. Two filtering nets 7 are provided on the two suspension collecting windows respectively. The two filtering nets 7 have different sizes, different installing positions and different apertures. Specifically, among the two filtering nets 7, one has a larger size and larger apertures, and is installed at a higher position, the other has a smaller size and smaller apertures, and is installed at a lower position. Hereinafter the filtering net 7 having a larger size will be referred as a first filtering net 7 while the other one will be referred as a second filtering net 7.

In operation, articles having sizes less than the apertures of the first filtering net 7 in the suspensions enter into the suspension collecting chamber 5 from the specimen tube 9 through the first filtering net 7, while under the liquid pressures, articles having sizes less than the aperture of the second filtering net 7 as well as liquid are discharged into the specimen tube 9 from the suspension collecting chamber 5 through the second filtering net 7. By repeating it, more articles with desired sizes will remain in the suspension collecting chamber 5, and the sampling needle 12 sucks the suspensions inside the specimen tube 9, specifically inside the suspension collecting chamber 5 in this embodiment, to accomplish the sampling operation. Therefore, the detection efficiency is improved.

In addition, as shown in FIGS. 4-6, a plurality of, e.g. two, extended plates 8 may be further included in the sampling member 1. The extended plates 8 may be perpendicular to respective side surfaces of the rectangular suspension collecting chamber 5 where the filtering nets 7 are located, i.e., where the suspension collecting windows are located. If the extended plates 8 are not provided, when the suspensions are stirred, the articles in the suspensions will pound the filtering nets 7, thus big articles may be held by the filtering nets 7 and thus block the filtering nets 7, which will affect collection of articles to be detected. In contrast, with the extended plates 8 which are perpendicular to respective side surfaces of the rectangular suspension collecting chamber 5 where the filtering nets 7 are located, since the rotation direction of the suspensions are the same as that of the extended plates 8 meanwhile the extended plates 8 are respectively positioned ahead of the respective filtering nets 7 in the rotation direction, the extended plates 8 will endure the pounding of the articles, so that the impact and velocity of suspensions at the filtering nets 7 are reduced. In this way, blocking of the filtering nets 7 by impact of the suspension is prevented or substantially prevented.

Furthermore, the extended plates 8 facilitate stirring of suspensions since they extend from the side wall of the sampling member 1. Also, when the sampling member 1 is rotated, with the help of the extended plates 8, the formed elements in the suspensions can enter the suspension collecting chamber 5 due to vortexes produced by the suspensions, and big articles will move with the vortexes, which prevents blocking of the filtering nets 7 by the big articles.

A film may be further disposed on the through hole 3 to seal the through hole 3 from the external environment. The film is preferably a soft film and easy to penetrate, but this invention is not limited thereto. In this case, after sucking the dilution solutions, the sampling needle 12 penetrates the film disposed on the through hole 3, and then injects the dilution solutions into the specimen tube 9. It could be understood that if the suspension collecting chamber 5 is provided, the sampling needle 12 will inject the dilution solutions into the suspension collecting chamber 5 of the sampling member 1 which is located inside the specimen tube 9.

Figure 7:
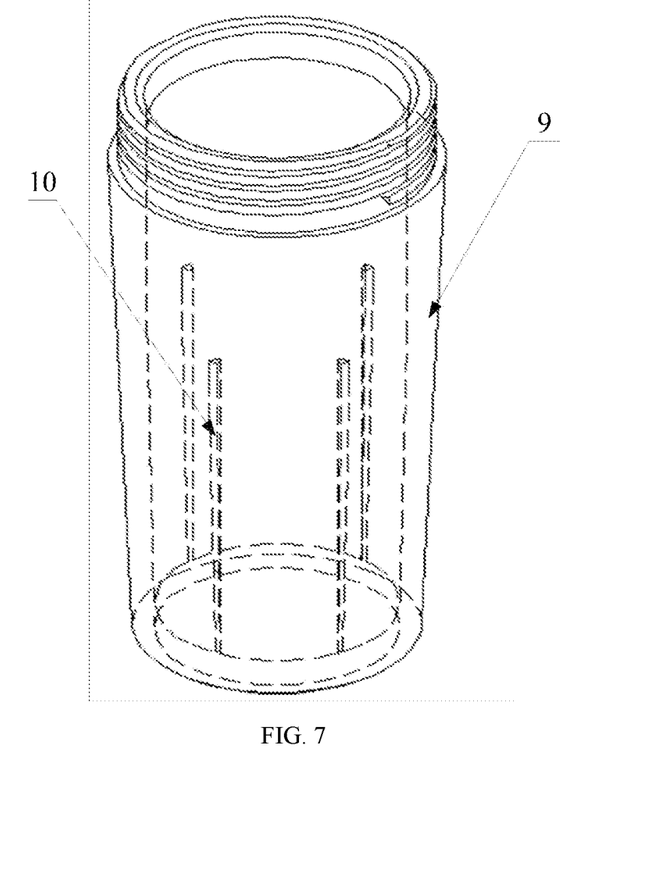
FIG. 7 is a schematic view illustrating a structure of a specimen tube.

FIG. 7 is a schematic view illustrating a structure of a specimen tube. As shown in FIG. 7, a plurality of protrusion ribs 10 are disposed on an inner wall of the specimen tube 9. The protrusion ribs 10 transversely protrude from the inner wall of the specimen tube and extend along a longitudinal axis of the specimen tube 9. In this way, the protrusion ribs 10 can block the suspensions to facilitate uniformity of stirring of the suspensions, and thus the stirring effect of the dilution and filtration device is improved.

In another embodiment of the present invention, the sampling member 1 comprises a collecting end 11 which is located opposite to the end of the sampling member 1 where the connecting cylinder 4 is connected, i.e., at a bottom end of the sampling member 1. The collecting end 11 may be used to collect specimens. Preferably, the collecting end 11 has a shape of a three-edged rule. That is, the collecting end 11 has three flat plates which are connected to each other at a same straight line, and angles between each two of the three flat plates are identical. With the collecting end 11 having the shape of the three-edged rule, it is convenient for the sampling member 1 to collect the specimens without pollution inside the excrements, and it is convenient to smash the specimens attached at the collecting end 11, so as to increase the uniformity of suspensions. But this invention is not limited thereto, in other embodiments, the collecting end 11 may have another shape, such as a ladle shape, a tooth shape, a brush shape or a mace shape.

An apparatus of preparing excrement detection solutions is also provided according to an embodiment of the present invention. The apparatus of preparing excrement detection solutions comprises a dilution and filtration device as described above and a stirring and sampling device which will be described hereinafter.

Figure 8:
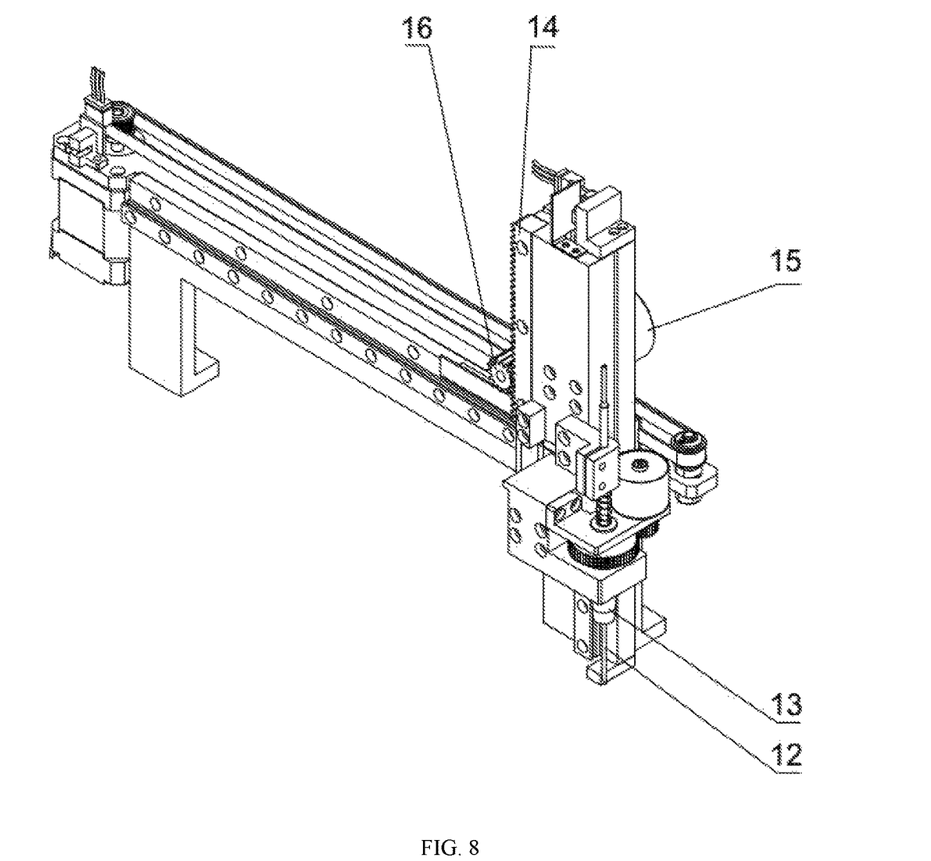
FIG. 8 is a schematic view illustrating a structure of a stirring and sampling device according to an embodiment of the present invention.

FIG. 8 is a schematic view illustrating a structure of a stirring and sampling device according to an embodiment of the present invention.

As shown in FIG. 8, the stirring and sampling device comprises a stirring part, the sampling needle 12 and a vertical movement part. The stirring part comprises the cylinder stirring handle 13 which has a shape matching the inner shape of the connecting cylinder 4, i.e., the inner shape of the hollow chamber of the connecting cylinder 4, so as to be connected thereto. The connecting method may be any of conventional connecting methods, such as via cooperation of protrusions and grooves, provided that rotation of the stirring handle 13 will drive the connecting cylinder 4 to rotate.

The sampling needle 12 is connected to the vertical movement part via the cylinder stirring handle 13, and thus can be moved vertically with driving of the vertical movement part. The stirring handle 13 may have a shape of cylinder, and is connected to the stirring part via a fixed shaft. That is, the fixed shaft is disposed between the stirring part and the stirring handle 13 in the vertical direction. The stirring handle 13 has an inner chamber which is interconnected with an inner chamber of the fixed shaft, so that the sampling needle 12 can pass through the inner chambers of the fixed shaft and the stirring handle 13. In addition, the vertical movement part comprises a vertical driving motor 15, a rack 14 driven by the vertical driving motor 15 and a transmission gear 16 engaged with the rack 14. The vertically driving motor 15 drives the vertical movement part to move vertically via cooperation of the rack 14 and the transmission gear 16.

Hereinafter a method of preparing excrement detection solutions will be described.

Firstly, the sampling member 1 is mounted on the top cap 2 via cooperation of the connecting cylinder 4 of the sampling member 1 and the through hole 3 of the top cap 2. That is, the connecting cylinder 4 is mounted to the sampling member 1 and the through hole 3 of the top cap 2, so that the sampling member 1 is mounted on the top cap 2. The sampling member 1 is rotatable with respect to the through hole 3.

Secondly, the excrement specimens are collected by the sampling member 1 mounted on the top cap 2, and the sampling member 1 to which the collected excrement specimens are attached is placed into the specimen tube 9. And then the top cap 2 and the specimen tube 9 are connected, e.g., threaded connected.

Thirdly, the sampling needle 12 passes through the connecting cylinder 4 and injects the dilution solutions inside the specimen tube 9. In the case of the suspension collecting chamber 5 being provided, the dilution solutions will be injected into the suspension collecting chamber 5 of the sampling member 1 which is located inside the specimen tube 9, otherwise the dilution solutions will be injected into the specimen tube 9 directly.

Then, a stirring handle 13 is inserted into the connecting cylinder 4 and is connected to the connecting cylinder 4. With rotation of the stirring handle 13, the sampling member 1 is driven to rotate along its own vertical axis, so that the suspensions are pushed to be rotated also. In the case of the extended plates 8 being provided, the suspension will be pushed by the extended plates 8 so as to rotate. During rotation of the suspensions, the extended plates 8 are always positioned in front of the filtering nets 7 in the rotation direction, so that blocking of the filtering nets 7 by impact of the suspension is prevented or substantially prevented.

Lastly, during rotation of the suspensions, the sampling needle 12 is inserted through the connecting cylinder 4 and sucks the suspensions inside the specimen tube 9, thus the excrement detection solution is obtained. In the case of the suspension collecting chamber 5 being provided, the sampling needle 12 will be inserted into the suspension collecting chamber 5 and sucks the suspensions in the suspension collecting chamber 5, otherwise the sampling needle 12 will be inserted in the specimen tube 9 directly and sucks the suspensions in the specimen tube 9.

It should be understood that the embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims and their equivalents.

What is claimed is:

1. A dilution and filtration device, comprising:
   a sampling member comprising a suspension collecting chamber having at least one suspension collecting window disposed at a side surface of the suspension collecting chamber;
   a top cap having a through hole at a center portion of the top cap;
   a connecting cylinder disposed at a top end of the sampling member and mounted to a side wall of the through hole of the top cap such that the connecting cylinder is concentric with the through hole and is rotatable;
   a specimen tube connected to the top cap and accommodating the sampling member; and
   a blocking member which is disposed at the top end of the sampling member and below the connecting cylinder.

2. The dilution and filtration device of claim 1, further comprising at least one filtering net disposed at the at least one suspension collecting window.

3. The dilution and filtration device of claim 2, wherein the sampling member further comprises at least one extended plate which is perpendicular to the side surface of the suspension collecting chamber where the at least one suspension collecting window is located.

4. The dilution and filtration device of claim 3, wherein the suspension collecting chamber has a shape of a hollow rectangle, the sampling member comprises two suspension collecting windows disposed at opposite side surfaces of the suspension collecting chamber respectively and two extended plates which are perpendicular to the two opposite side surfaces of the suspension collecting chamber where the two suspension collecting windows are located respectively.

5. The dilution and filtration device of claim 4, wherein the dilution and filtration device comprises two filtering nets disposed at the two suspension collecting windows respectively.

6. The dilution and filtration device of claim 5, wherein one filtering net has a larger size and larger apertures and is disposed at a higher position while the other filtering net has a smaller size and smaller apertures and is disposed at a lower position.

7. The dilution and filtration device of claim 1, wherein the top cap and the specimen tube are connected to each other by thread.

8. The dilution and filtration device of claim 1, wherein the specimen tube comprises a plurality of protrusion ribs transversely protruding from an inner wall of the specimen tube and extending along a longitudinal axis of the specimen tube.

9. The dilution and filtration device of claim 1, wherein the sampling member further comprises a collecting end disposed at a bottom end of the sampling member.

10. The dilution and filtration device of claim 1, wherein the connecting cylinder and the blocking member are detachably connected to the sampling member.

11. The dilution and filtration device of claim 10, wherein the connecting cylinder and the blocking member are connected to the sampling member in a clamping manner.

12. An apparatus of preparing excrement detection solutions, comprising:
 a dilution and filtration device, comprising:
  a sampling member comprising a suspension collecting chamber having at least one suspension collecting window disposed at a side surface of the suspension collecting chamber;
  a top cap having a through hole at a center portion of the top cap;
  a connecting cylinder disposed at a top end of the sampling member and mounted to a side wall of the through hole of the top cap such that the connecting cylinder is concentric with the through hole and is rotatable; and
  a specimen tube connected to the top cap and accommodating the sampling member, and
 a stirring and sampling device, comprising:
  a vertical movement part comprising a vertical driving motor, a rack driven by the vertical driving motor and a transmission gear engaged with the rack;
  a stirring part connected to the vertical movement part and comprising a cylinder stirring handle which has a shape matching an inner shape of the connecting cylinder; and
  a sampling needle passing through an inner chamber of the cylinder stirring handle and connected to the vertical movement part.

13. The apparatus of claim 12, wherein the stirring part further comprises a fixed shaft disposed between the cylinder stirring handle and the vertical movement part, and the sampling needle further passes through an inner chamber of the fixed shaft.

14. The apparatus of claim 12, wherein the sampling member further comprises at least one extended plate which is perpendicular to the side surface of the suspension collecting chamber where the at least one suspension collecting window is located.

15. The apparatus of claim 14, wherein the sampling member comprises a plurality of suspension collecting windows disposed at side surfaces of the suspension collecting chamber, and a plurality of extended plates which are perpendicular to the side surfaces of the suspension collecting chamber where the plurality of suspension collecting windows are located respectively.

16. A method of preparing excrement detection solutions using a dilution and filtration device, the dilution and filtration device comprising:
 a sampling member comprising a suspension collecting chamber having at least one suspension collecting window disposed at a side surface of the suspension collecting chamber;
 a top cap having a through hole at a center portion of the top cap;
 a connecting cylinder disposed at a top end of the sampling member and mounted to a side wall of the through hole of the top cap such that the connecting cylinder is concentric with the through hole and is rotatable;
 a specimen tube connected to the top cap and accommodating the sampling member; and
 a blocking member which is disposed at the top end of the sampling member and below the connecting cylinder, the method comprising:
 mounting the connecting cylinder to the sampling member and the side wall of the through hole of the top cap;
 collecting excrement specimens by the sampling member, placing the sampling member into the specimen tube, and connecting the specimen tube to the top cap;
 injecting dilution solutions into the suspension collecting chamber and stirring suspensions formed by mixing of the excrement specimens and the dilution solutions; and
 sucking the suspensions during stirring from the suspension collecting chamber to obtain the excrement detection solutions.

* * * * *